US00PP15746P2

(12) United States Plant Patent
Hutchins

(10) Patent No.: US PP15,746 P2
(45) Date of Patent: May 3, 2005

(54) ***HEBE* PLANT NAMED 'CLEAR SKIES'**

(50) Latin Name: ***Hebe* hybrid**
*(H. pimeleoides×H. albicans)*
Varietal Denomination: Clear Skies

(76) Inventor: Graham Hutchins, 384 Wingette Lane, Hornchurch, Essex (GB), RM 11 3BU ( * ) Notice: Subject to any disclaimer, the term of this patent is extended or adjusted under 35 U.S.C. 154(b) by 15 days.

(21) Appl. No.: 10/404,721

(22) Filed: Mar. 31, 2003

(51) Int. Cl.[7] ..... A01H 5/00
(52) U.S. Cl. ..... Plt./226
(58) Field of Search ..... Plt./226

*Primary Examiner*—Howard J. Locker

(57) ABSTRACT

A new cultivar of *Hebe* plant named 'Clear Skies' that is characterized by a compact, upright habit, steel-blue foliage and violet-blue flowers in summer. In combination these traits set 'Clear Skies' apart from all other existing varieties of *Hebe* known to the inventor.

2 Drawing Sheets

Genus: *Hebe.*
Species: Hybrid (*H. pimeleoides×H. albicans*).
Denomination: Clear Skies.

BACKGROUND OF THE INVENTION

The present invention relates to a new and distinct cultivar of *Hebe* which is grown as an evergreen shrub and used as an ornamental container plant and a landscape plant. The new cultivar is known botanically as *Hebe* 'Clear Skies' and will be referred to hereinafter by the cultivar name 'Clear Skies'.

'Clear Skies' resulted from a formal breeding program developed by the inventor to produce new cultivars of *Hebe* plants that are distinct from the existing varieties. 'Clear Skies' was bred in a cultivated area of Essex, United Kingdom and selected by the inventor in 1995. The new cultivar 'Clear Skies' is a hybrid plant that resulted from open pollination. The female parent is the unpatented variety *Hebe pimeleoides glauco-caerulea,* and the male parent is presumed to be an unnamed and unpatented *Hebe albicans* plant. 'Clear Skies' is considered by the inventor to be a true interspecific hybrid.

When compared with the female parent, 'Clear Skies' is distinguishable by its upright habit and a brighter foliage appearance. When compared with the presumed male parent plant, 'Clear Skies' is distinguishable by its silver-blue foliage. The foliage color of *Hebe albicans* is predominantly green or gray-green.

'Clear Skies' is an evergreen shrub that exhibits a compact, upright habit. The distinguishing traits that make 'Clear Skies' unique are steel-blue foliage, unique leaf shape and violet-blue flowers. The closest comparison plants are *Hebe pinguifolia* 'Pagei' (unpatented) and *Hebe* 'Blue Star' (unpatented). 'Clear Skies' differs from both of the comparison plants in foliage color, habit, and flower color.

The first asexual reproduction was conducted by the inventor, in a cultivated area of Essex, United Kingdom in March 1995. The method used for asexual propagation was softwood cuttings. Since that time, subsequent reproductions of 'Clear Skies' using softwood cuttings have established that the characteristics of the new cultivar remain stable and true to type in successive generations.

SUMMARY OF THE INVENTION

The following traits have been repeatedly observed and represent the characteristics of the new *Hebe* cultivar 'Clear Skies'. These traits in combination distinguish 'Clear Skies' from all other commercial varieties known to the inventor. 'Clear Skies' has not been tested under all possible conditions and phenotypic differences may be observed with variations in environmental, climatic and cultural conditions.

1. *Hebe* 'Clear Skies' exhibits a compact, upright habit.
2. *Hebe* 'Clear Skies' is an evergreen shrub.
3. *Hebe* 'Clear Skies' exhibits steel-blue colored foliage.
4. *Hebe* 'Clear Skies' exhibits violet-blue flowers.
5. *Hebe* 'Clear Skies' is propagated using softwood cuttings.
6. *Hebe* 'Clear Skies' is 60 cm. in width and 40 cm. in height at maturity.
7. *Hebe* 'Clear Skies' is an ornamental suitable for containers such as tubs, and for use in the landscape.
8. *Hebe* 'Clear Skies' is hardy to minus 8° Centigrade.

BRIEF DESCRIPTION OF THE DRAWINGS

The accompanying color drawings illustrate the overall appearance of the new cultivar 'Clear Skies' showing the colors as true as it is reasonably possible to obtain in colored reproductions of this type. Colors in the photographs may differ from the color values cited in the detailed botanical description, which more accurately describe the actual colors of the new cultivar 'Clear Skies'.

The drawing on sheet 1 illustrates the plant from a top perspective.

The drawing on sheet 2 is a close-up view of the flowers.

The drawings were made using conventional techniques and although colors may appear different from actual colors due to light reflectance they are as accurate as possible by conventional photography.

BOTANICAL DESCRIPTION OF THE PLANT

The following is a detailed description of 18-month-old plants in 1-liter containers grown out-of-doors in Arroyo Grande, Calif. The color determinations are in accordance with The 2001 Royal Horticultural Society Colour Chart of The Royal Horticultural Society London, England, except where general color terms of ordinary dictionary significance are used. Growing conditions, diseases and pests are similar to that of other *Hebe*.

Botanical classification: *Hebe* hybrid 'Clear Skies'.
Commercial classification: Ornamental shrub.
Use: For use in tubs, and in the landscape.
Cultural requirements: Plant in full sun and fast draining soil with regular water. Plant in partial shade in hot climates.
Parentage: *Hebe* 'Clear Skies' is a hybrid plant that resulted from open pollination of the following female parent plant and presumed male parent plant:
- *Female parent.*—*Hebe pimeleoides* var. *glauco-caerulea* (not patented).
- *Presumed male parent.*—An unnamed, unpatented *Hebe albicans* plant.

Plant description:
- *Bloom period.*—May and June in the United Kingdom; April to September in the U.S. Pacific North West and in coastal California.
- *Plant habit.*—Compact, upright habit.
- *Branching habit.*—Freely branching from lower stem. Apical branches ascending unbranched until branching occurs at 5 cm to 10 cm from apex.
- *Vigor.*—Slow-growing.
- *Plant dimensions* (*in 1-liter container*).—39 cm. in width and 20 cm. in height.
- *Plant dimensions* (*at maturity*).—60 cm. in width and 40 cm. in height.
- *Hardiness.*—Hardy to minus 8° Centigrade.
- *Root system.*—Fibrous.
- *Propagation.*—Propagation is accomplished using soft-wood cuttings.
- *Time to develop roots.*—4 weeks at 16–18° Centigrade air temperature.
- *Crop time.*—A minimum of 14 months is needed to produce a finished 1-liter container.
- *Disease and pest problems.*—Plant is susceptible to root rot in any poor-draining soil.

Stem:
- *Stem shape.*—Cylindrical.
- *Stem dimensions.*—16 cm. in length and 4 mm. in width.
- *Stem color* (*new growth*).—138B.
- *Stem color* (*mature stem*).—200B on stem itself and with a dry thin peeling surface over stem that is 201B.
- *Internodes.*—5 mm. between nodes.
- *Leaf scars.*—Present at base of stems.
- *Leaf scar dimensions.*—4 mm. in width and less than 0.50 mm. in depth.
- *Leaf scar color.*—199C.
- *Amount of leaf scars.*—Numerous.
- *Stem surface.*—Dry, thin, scarious surface that is the color 201B.

Foliage:
- *Type.*—Evergreen, remains unchanged in appearance year-round.
- *Arrangement.*—Opposite.
- *Shape.*—Obovate.
- *Curvature.*—Concave.
- *Margins.*—Entire and slightly involute.
- *Apex.*—Sub-acute.
- *Base.*—Truncate.
- *Midrib* (*upper surface*).—Depressed, slight groove.
- *Midrib* (*lower surface*).—Thickened (slightly protruding).
- *Midrib color.*—(Adaxial surface): N189B.
- *Midrib color.*—(Abaxial surface): N189A.
- *Leaf dimensions.*—1.50 cm. in length and 0.75 cm. in width.
- *Texture.*—Leathery.
- *Attachment.*—Sessile, slightly decurrent.
- *Leaf aspect.*—Generally slightly erect, tending to semi-erect towards apex.
- *Leaf bud shape.*—Terete.
- *Leaf surfaces* (*adaxial and abaxial*).—Glaucous.
- *Leaf margins.*—Slightly thickened, rounded edge, smooth, entire.
- *Leaf color* (*abaxial surface*).—189A.
- *Leaf color* (*adaxial surface*).—N189B.
- *Fragrance.*—Absent.

Flowers:
- *Bud shape.*—Elliptic cone.
- *Bud color.*—Violet blue 95C.
- *Bud surface.*—Smooth.
- *Bud dimensions.*—2.5 mm. in diameter and 8 mm. in length.
- *Shape of corolla tube.*—Tubular in shape.
- *Corolla dimensions.*—3 mm–4 mm in length, 2 mm diameter at the mouth.
- *Surface of corolla tube.*—Smooth.
- *Corolla tube color.*—The overall color ranges from violet blue 95C (flowers freshly open) to paler blue 97C (flowers aged).
- *Flower dimensions* (*calyx, corolla tube, and lobes*).—1.0–1.5 cm. in length and 1.0–1.5 cm. in diameter.
- *Number of corolla lobes.*—Four.
- *Number of petals.*—Four in number.
- *Petal dimensions* (*excluding corolla*).—5 mm in length and 3 mm in width.
- *Petal apex shape.*—Obtuse.
- *Color of petals.*—The overall color ranges from violet blue 95C (flowers freshly open) to paler blue 97C (flowers aged).
- *Petals fused or unfused.*—Petals are basally fused.
- *Shape of petals.*—Spatulate.
- *Flower aspect.*—Facing outward.
- *Inflorescence form.*—Raceme.
- *Flower arrangement.*—Flowers are arranged in whorls, as is typical of the species and its known cultivars.
- *Flower development.*—In clusters, commencing at base of raceme.
- *Quantity of flowers.*—A range of 25–35 flowers per whorl and a range of 20–40 whorls on a second year plant.
- *Fragrance.*—Not observed.
- *Peduncle dimensions.*—2 mm. in diameter and 10 mm–15 mm in length.
- *Peduncle shape.*—Cylindrical.
- *Peduncle surface.*—Smooth.
- *Peduncle color.*—138A.
- *Calyx.*—Absent.
- *Number of sepals.*—Four.
- *Fused or unfused.*—Basally fused.
- *Sepal color.*—Greener than leaves, approximately 191A.
- *Sepal apex.*—Obtuse.
- *Sepal surface.*—Lightly pubescent.

Reproductive organs:

*Stigma shape.*—Narrowly capitate.

*Stigma dimensions.*—Approximately 0.2 mm. in width.

*Stigma color.*—Yellow.

*Style shape.*—Filiform.

*Style dimensions.*—Approximately 5 mm–7 mm in length and 0.2 mm in width.

*Style color.*—White.

*Stamens.*—Two in number, slightly diverging, fused at the base, creating a V-shape.

*Dimensions of stamens.*—The stamens are 8 mm–10 mm in length and less than 1 mm. in width. Stamens are exserted by approximately 5 mm.

*Color of filament.*—97C (all flower ages).

*Anther shape and dimensions.*—Apiculate: 1.6 mm in length and 1.2 mm. in width.

*Anther color.*—Gray-orange, approximately 165D.

*Pollen.*—Pale purple.

*Ovary shape and position.*—Ovoid, Inferior.

*Ovary dimensions.*—Approximately 2 mm long and 1.5 mm in width.

Seed: No seed has been observed.

It is claimed:

1. A new and distinct cultivar of *Hebe* plant named 'Clear Skies' as described and illustrated herein.

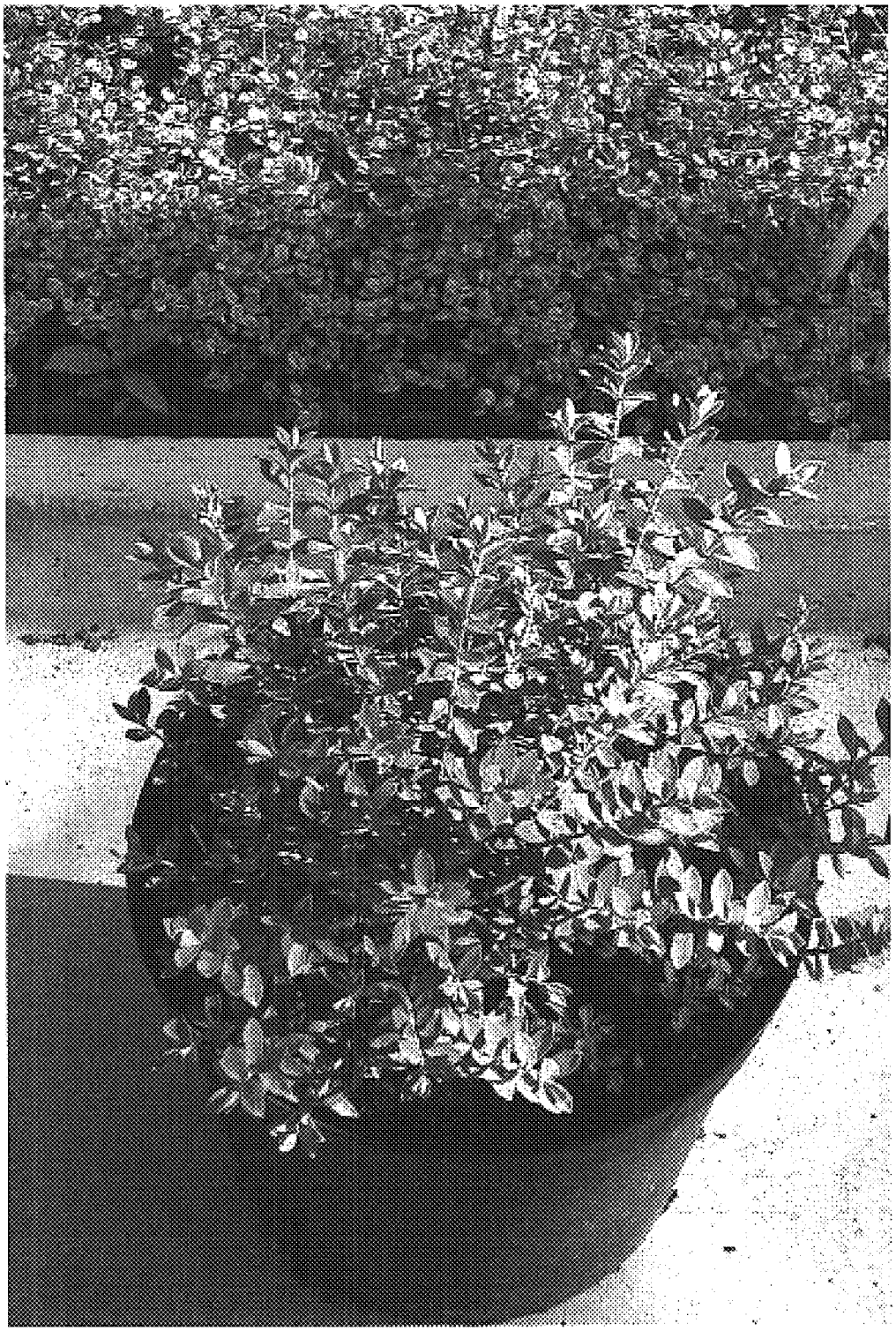

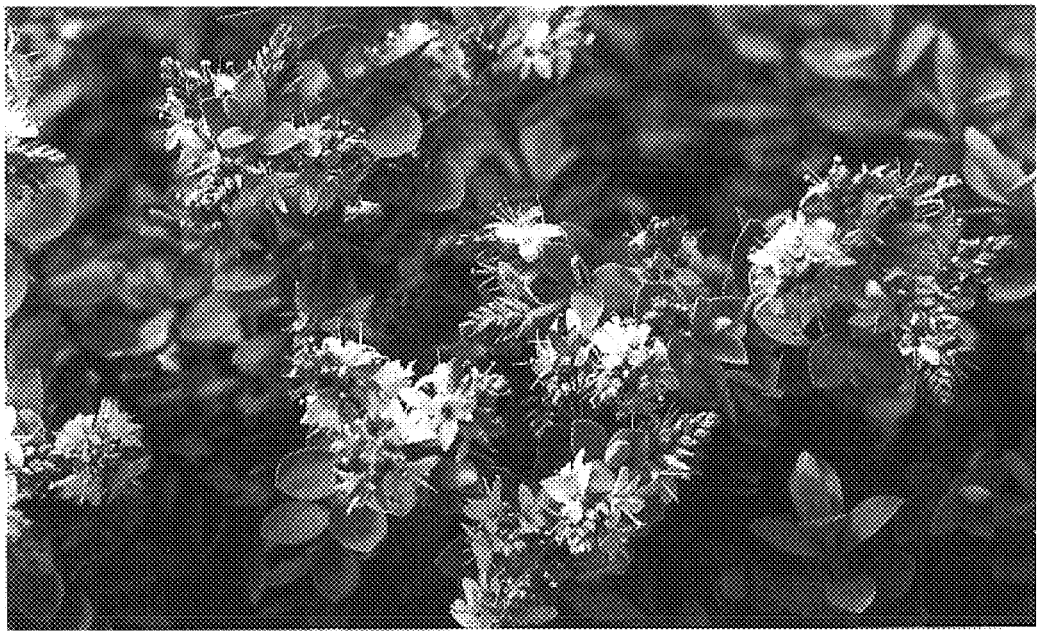

* * * * *